United States Patent
Gray et al.

(10) Patent No.: US 6,503,062 B1
(45) Date of Patent: Jan. 7, 2003

(54) METHOD FOR REGULATING FLUID PUMP PRESSURE

(75) Inventors: Larry Gray, Merrimack, NH (US); Robert Bryant, Manchester, NH (US)

(73) Assignee: Deka Products Limited Partnership, Manchester, NH (US)

( * ) Notice: Subject to any disclaimer, the term of this patent is extended or adjusted under 35 U.S.C. 154(b) by 0 days.

(21) Appl. No.: 09/612,005

(22) Filed: Jul. 10, 2000

(51) Int. Cl.[7] .......................... F04B 43/06; A61M 31/00
(52) U.S. Cl. .............................. 417/53; 417/395; 604/67
(58) Field of Search ......................... 417/53, 279, 395; 604/67

(56) References Cited

U.S. PATENT DOCUMENTS

| | | | | |
|---|---|---|---|---|
| 4,468,219 A | * | 8/1984 | George et al. ............. | 604/67 |
| 4,778,451 A | | 10/1988 | Kamen ...................... | 604/67 |
| 4,808,161 A | * | 2/1989 | Kamen ...................... | 604/67 |
| 4,976,162 A | | 12/1990 | Kamen ...................... | 73/865.9 |
| 5,088,515 A | | 2/1992 | Kamen ...................... | 137/15 |
| 5,178,182 A | | 1/1993 | Kamen ...................... | 137/454.2 |
| 5,207,645 A | * | 5/1993 | Ross et al. ................. | 604/67 |
| 5,628,908 A | | 5/1997 | Kamen et al. ............. | 210/646 |
| 5,795,328 A | * | 8/1998 | Barnitz et al. ............ | 604/67 |

* cited by examiner

Primary Examiner—Michael Koczo
(74) Attorney, Agent, or Firm—Bromberg & Sunstein LLP

(57) ABSTRACT

A method is provided for regulating fluid pump pressures by detecting an elevation differential between a fluid flow control device and the distal end of a fluid line in communication with the fluid flow control device. A fluid flow control device, for instance a peritoneal dialysis device, is at a first height, a distal end of a fluid line is at a second height, and a valved outlet, when open, affords communication between the fluid flow control device and the distal end of the fluid line. The elevation differential is correlatable with a pressure measurable during a calibration procedure provided as a part of the methodology.

26 Claims, 7 Drawing Sheets

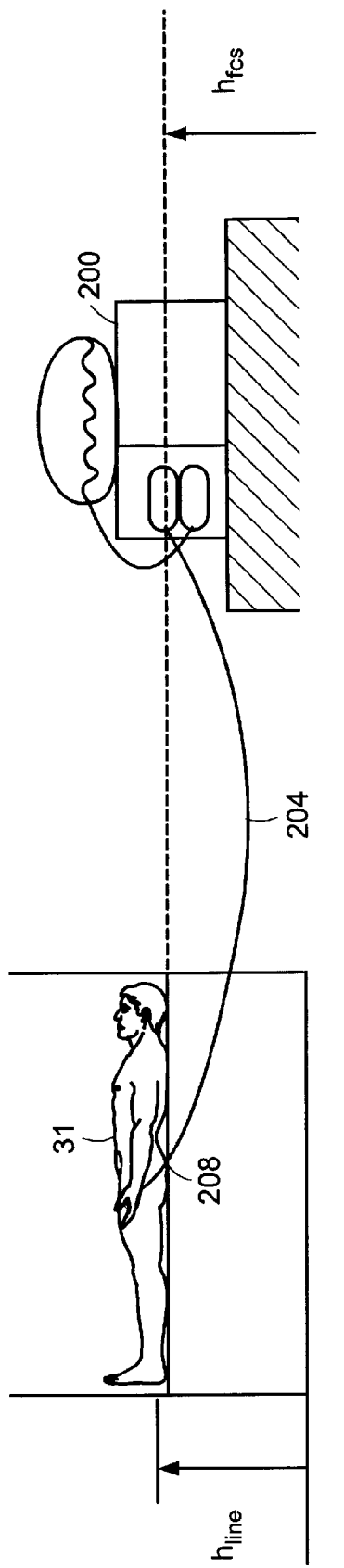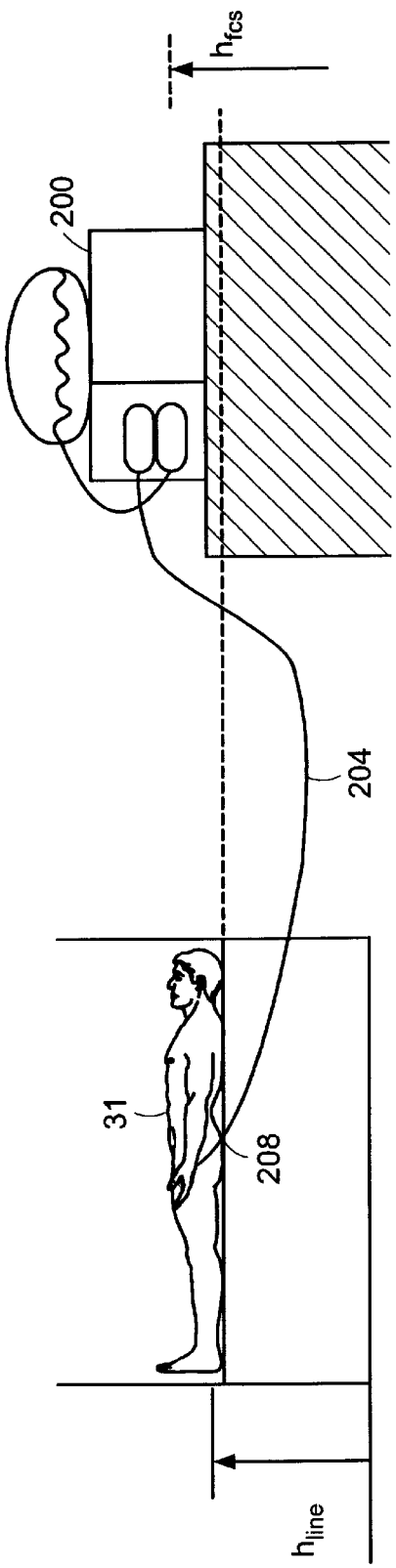
FIG. 3a
FIG. 3b

METHOD FOR REGULATING FLUID PUMP PRESSURE

TECHNICAL FIELD

The present invention relates to fluid flow control devices and, more specifically, to regulating pump pressures. In particular, the invention provides a method and apparatus for increasing the fluid flow rate in a fluid flow control device while maintaining desired pressure levels. The present invention also relates to systems that can determine the relative elevation of a pump with respect to a distal end of a line in communication with the pump.

BACKGROUND ART

A function of fluid flow control systems is to regulate the rate of distribution of transport fluid through a line. Some examples of fluid control devices are peritoneal dialysis machines and intravenous fluid delivery systems. Fluid flow control systems may include a permanent housing which does not come into direct contact with the transporting fluid and into which a fluid-exposed disposable cassette is placed. Flexible membranes, or other structures that respond to pressure, maintain separation between the permanent and disposable components. Examples of such control systems and their sub-components (in particular, valves) are disclosed in U.S. Pat. Nos. 4,778,451, 4,976,162, 5,088,515, and 5,178,182. These patents are all issued to Kamen and are all hereby incorporated herein by reference.

One problem with respect to fluid flow control devices arises in, for example dialysis treatment. Patients want to minimize the time spent hooked up to the peritoneal dialysis machine. In order to satisfy patient demands, the flow rate of the fluid pumped into the patient's catheter may be proportionally increased by increasing the pumping pressure. However, international specifications (for example, EN 50072) regulate the maximum and minimum pressures allowed in the patient's catheter. The maximum positive pressure allowable is set at 150 mm Hg (~3 psi), and the minimum (or maximum negative, or suction pressure) is set at −75 mm Hg (~−1.5 psi). Prior art dialysis machines use pumping pressures of about 75 mm Hg (1.5 psi) when pumping fluid into the patient. If the dialysis machine and the patient are at the same elevation, the pressure applied at the pump will be very close to the pressure at the patient's catheter. If, on the other hand, the dialysis machine is elevated above the patient, the pressure at the patient's catheter will be higher than the pressure applied at the pump. Consequently, to insure a margin of safety, the pumping pressure is set well below the maximum allowable pressure to compensate for any uncertainty in the position of the patient relative to the dialysis machine.

SUMMARY OF THE INVENTION

A method is provided for regulating fluid pump pressures based on the relative elevation between a fluid flow control device and a distal end of a fluid line by providing at least one liquid volume in valved communication with the distal end. The pressure measurement of the liquid volume is calibrated, and then valving is opened to establish communication between the liquid volume and the distal end of the fluid line. A pressure associated with the liquid volume is measured, and the fluid pump pressure is adjusted in accordance with the measured pressure.

Preferably, the fluid flow control device has two liquid volumes. A first liquid volume is in valved communication with a second liquid volume. The fluid line is preferably in valved communication with both liquid volumes. The pressures in the liquid volumes are calibrated, and communication between one liquid volume and the distal end of the fluid line is established. A pressure associated with the one liquid volume is measured, and the fluid pump pressure is adjusted in accordance with the measured pressure.

The fluid flow control device preferably includes a control volume for each liquid volume, a transducer for each control volume, and a processor for reading and storing pressure values, computing and identifying a correlation between pressure values, and calculating pressure values based on identified correlations. The processor may estimate the elevation differential based upon the pressure values, and/or regulate fluid pump pressures. The fluid flow control device may also include pressure means for pressurizing a liquid volume. The device may further include one of a wide variety of valve arrangements for controlling fluid communication between the liquid volumes and the distal end of the line. The processor may also control the valve arrangement, the means for pressurizing the liquid volume, and the fluid pump pressure.

In another preferred embodiment, the liquid volume and the control volume themselves are parts of a pump. Preferably, the pump includes a flexible membrane that divides the liquid volume and the control volume. In other embodiments, the fluid flow control device includes a pump.

In a preferred method for detecting the relative elevation between a first location and a second location, a fluid flow control device is provided at the first location with at least one membrane pump in valved communication with the second location. The membrane pump is isolated from the second location, and a pressure transducer of the membrane pump is calibrated. Valving is then opened to establish communication between the membrane pump and the second location. The pressure of the membrane pump is measured, and the relative elevation between the first location and the second location is estimated.

In a further embodiment, calibrating the pressure transducer may include filling the membrane pump with fluid in pressure equilibrium with the pressure at the first location, measuring a first calibration pressure of the membrane pump, filling the membrane pump with fluid in pressure equilibrium with a known (i.e., predetermined or measured) calibration pressure, and measuring a second calibration pressure of the membrane pump. The relative elevation between the first location and the second location may be estimated based on the known calibration pressure, the first calibration pressure, and the second calibration pressure.

BRIEF DESCRIPTION OF THE DRAWINGS

The invention will be more readily understood by reference to the following description, taken with the accompanying drawings, in which:

FIGS. 3(a) and 3(b) schematically illustrate the relationship between the relative elevation of the fluid flow control device and the pressure experienced at the distal end of a fluid line;

DETAILED DESCRIPTION OF SPECIFIC EMBODIMENTS

Figure 1:
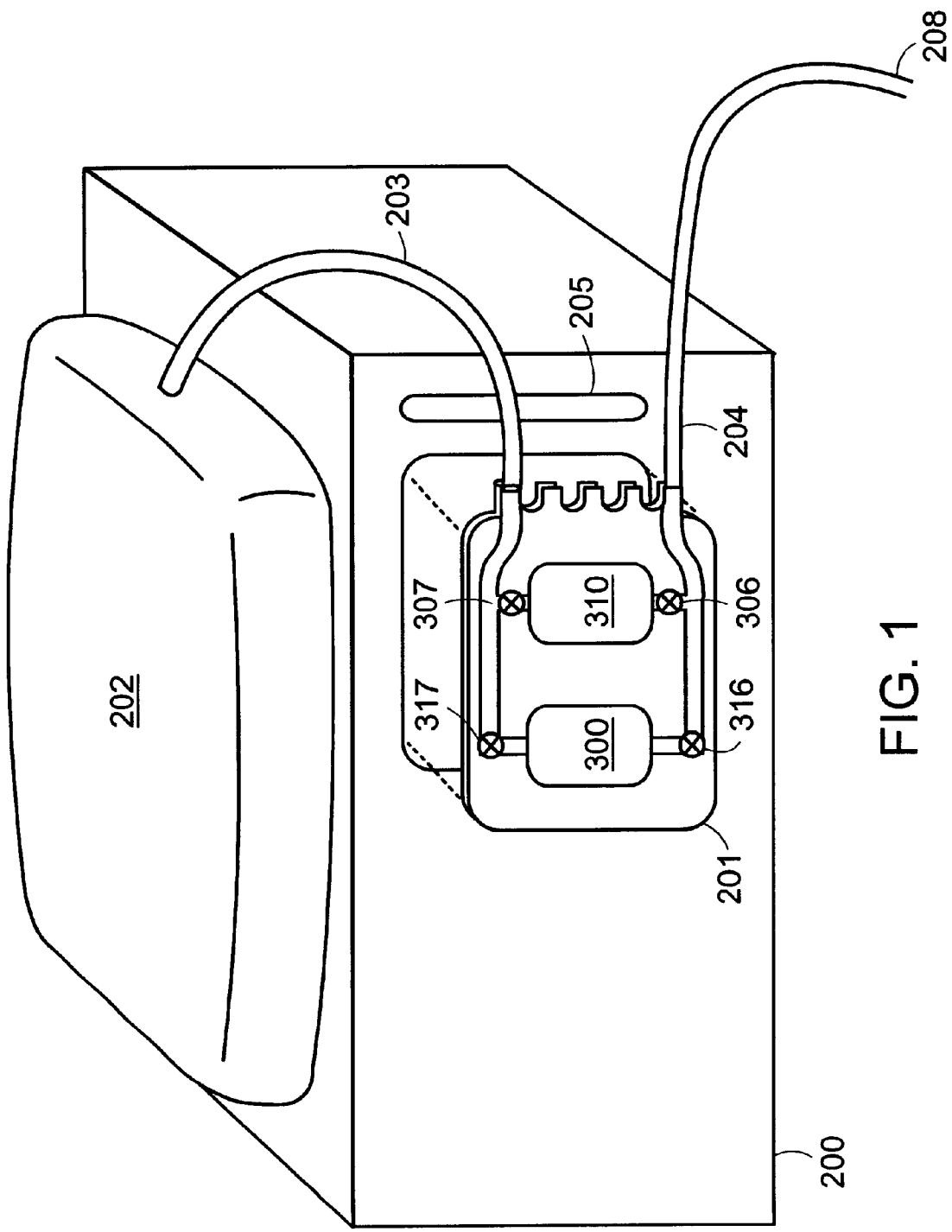
FIG. 1 is a perspective view of a prior art fluid flow control device.

FIG. 1 shows a prior art fluid flow control device 200. A disposable cassette 201 is securely mounted onto the fluid flow control device 200. Fluid communication with the cassette 201 is maintained from a heated solution bag 202 via a solution inlet line 203 and is also maintained to a distal end 208 of an outlet line 204. The fluid flow control device 200 has an occluder bar 205 that when activated by the fluid flow control device 200, occludes both the inlet line 203 and the outlet line 204. The fluid flow control device 200 is shown to have two pumps 300 and 310, each pump having inlet and outlet valves 306, 307, 316, and 317.

Figure 2:
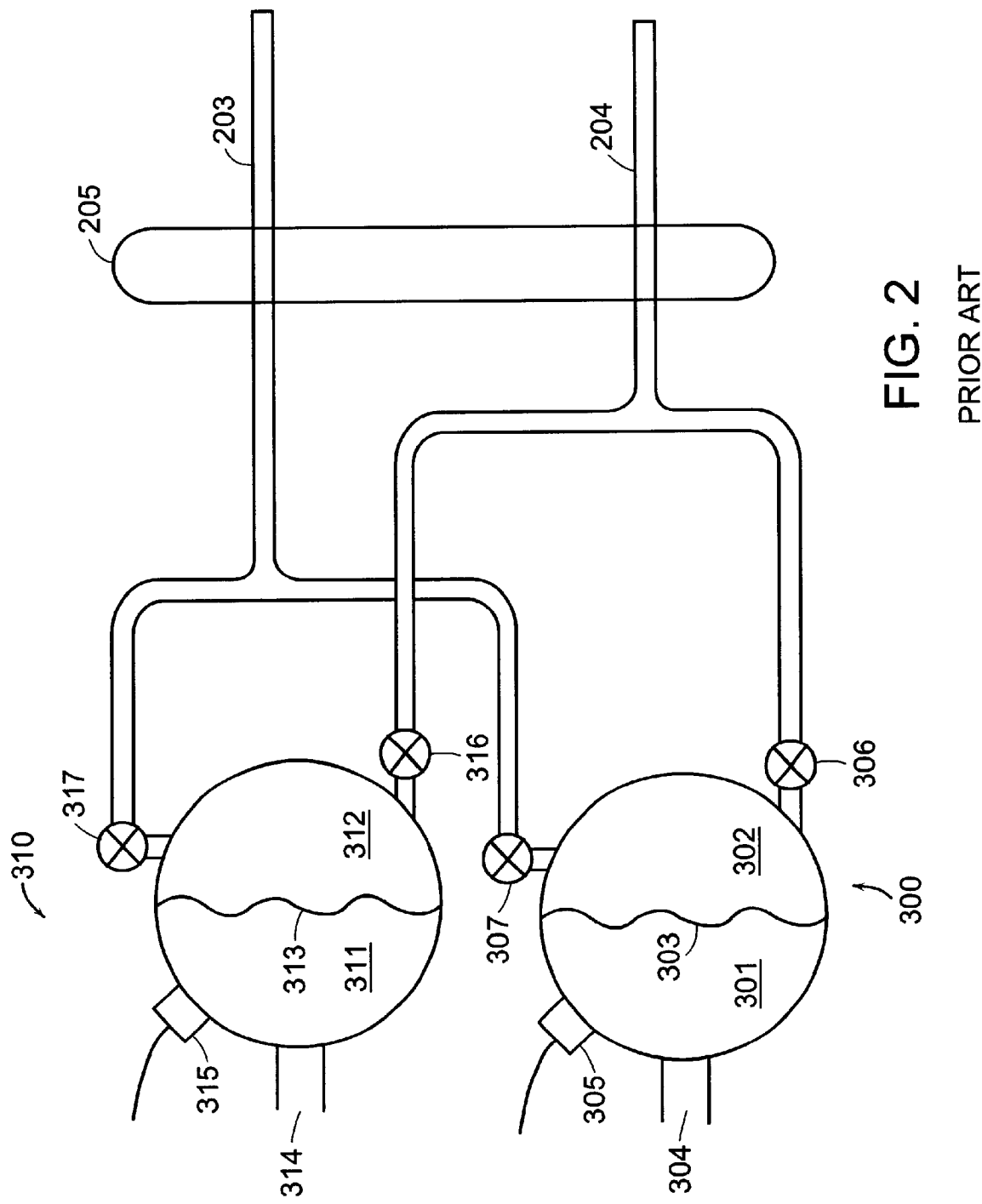
FIG. 2 illustrates a membrane-based fluid flow control system contained in the device of FIG. 1.

FIG. 2 illustrates a membrane-based fluid control flow system utilized in fluid flow control device 200 of FIG. 1 and having a first pump 300 and a second pump 310. Flexible membrane 303 is shown as dividing first pump 300 into a first control volume 301 and a first liquid volume 302. The first control volume 301 may be pressurized through a first pressure line 304. The pressure in the first control volume 301 is measured by a first pressure transducer 305 attached to and in fluid communication with the first control volume 301. Similarly, flexible membrane 313 divides second pump 310 into a second control volume 311 and a second liquid volume 312. The second control volume 311 may be pressurized through a second pressure line 314. The pressure in the second control volume 311 is measured by a second pressure transducer 315 attached and in fluid communication with the second control volume 311. Pressurizing may occur through the use of a control gas or liquid, or other methods known in the art, such as pumps, pistons, pressurized reservoirs, valves, and vents. As noted above these pressurizing devices are explained in greater detail in the U.S. Patents issued to Kamen and incorporated herein by reference.

A first outlet valve 306 controls the outlet flow from the first liquid volume 302 to the outlet line 204 and a second outlet valve 316 controls the outlet flow from the second liquid volume 312 to the outlet line 204. The outlet flows from the first pump 300 and second pump 310 are, therefore, in fluid communication with each other and with the distal end 208 (see FIG. 1) of the outlet line 204. A first inlet valve 307 controls the inlet flow into the first liquid volume 302, and a second inlet valve 317 controls the inlet flow into the second liquid volume 312. The inlet flows from the first pump 300 and the second pump 310 are in fluid communication with each other and with the heated solution bag 202 through solution inlet line 203. When activated, the occluder bar 205 isolates both the outlet line 204 and the solution bag 202 from the pumps 300 and 310 while allowing fluid communication between the two pumps 300 and 310 when either or both sets of valves are open.

FIG. 3(a) schematically illustrates a fluid line 204 in communication with a subject 31 at the same elevation as a fluid flow control device 200. When the distal end 208 of the line 204 and the fluid flow control device 200 are at the same elevation, the pressure at the distal end 208 of the line 204 is equal to the pressure in the fluid flow control device 200. FIG. 3(b) schematically illustrates a subject 31 at a lower elevation to that of fluid flow control device 200. When this situation occurs, the pressure in the distal end 208 of the line 204 is greater than the pressure in the fluid flow control device 200. If, for example, the fluid flow control device 200 is a peritoneal dialysis machine, the relationship between the relative elevation and the pressure differential may be calculated. A 0.3 m (one foot) elevation difference between the patient and the dialysis machine results in about 25 mm Hg (0.5 psi) difference between the pressure in the dialysis machine and the pressure in the catheter attached to the patient. Clearly, the lower the patient is in relation to the dialysis machine, the greater the pressure will be in the catheter. Therefore, for the example discussed above, if it were possible to determine the relative elevation of the patient with respect to the dialysis machine, the pumping pressure could be decreased to maintain a margin of safety. Conversely, for the above example, the fluid could be safely withdrawn from the patient at a lower pressure (higher negative pressure) and still maintain the same margin of safety.

Figure 4:
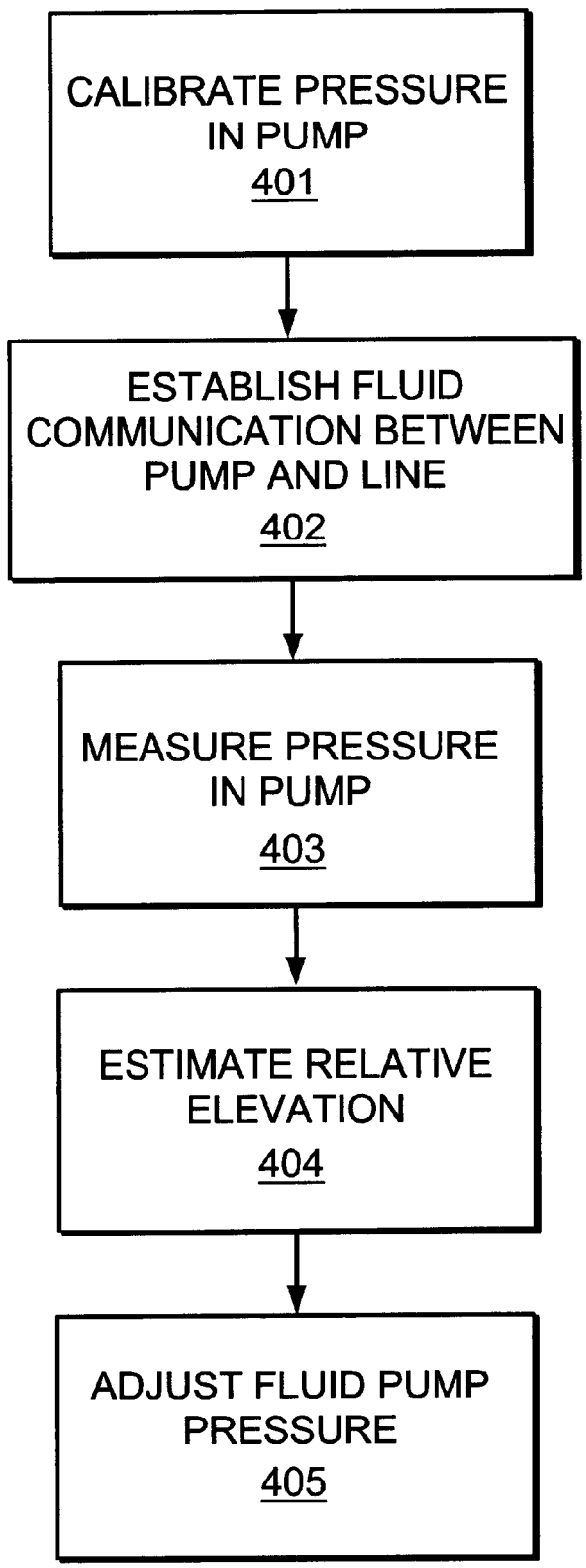
FIG. 4 is a block diagram illustrating the process of detecting the relative elevation and regulating fluid pump pressure according to one embodiment of the present invention.

FIG. 4 is a block diagram illustrating the process of detecting the relative elevation and regulating the fluid pump pressure according to one embodiment of the present invention. In this embodiment, the fluid flow control system of FIG. 2 is employed. The pressure of at least one of the pumps 300 and 310 is correlated with that of the pressure at the distal end 208 of the fluid line 204, which, in turn may be related to the elevation differential. The correlation is complicated due to the fact that, in membrane based systems, the flexible membranes 303 and 313 store some of the pV work as elastic energy resulting in slightly different pressures across the membrane at equilibrium. Therefore, the invention provides for measurements, correlation, and the development of relationships prior to measuring the relative elevation. Without such correlation, the estimate of the relative elevation could be in error by as much as eight to ten inches. The inventors have discovered that new membranes in such systems exhibit hysteresis. Such hysteresis appears to diminish as the membranes are repeatedly flexed. Therefore, the calibration may be performed after other startup procedures that flex the membrane are completed.

Referring to FIG. 2 for the various referenced items, the pressure in at least one pump 300 or 310 is calibrated in process 401. In process 402, fluid communication is established between the at least one pump 300 or 310 and the line 204. The static pressure in the pump in communication with the line is measured in process 403, and the reactive elevation between the line and the fluid flow control device is estimated in process 404. This is accomplished by using the static pressure measured in the pump and by using a known relationship between a height differential and pressure differential (e.g., 0.3 m (1 foot) per 25 mm Hg.) Finally, the pump pressure may be adjusted to accommodate the height differential in process 405.

Figure 5A:
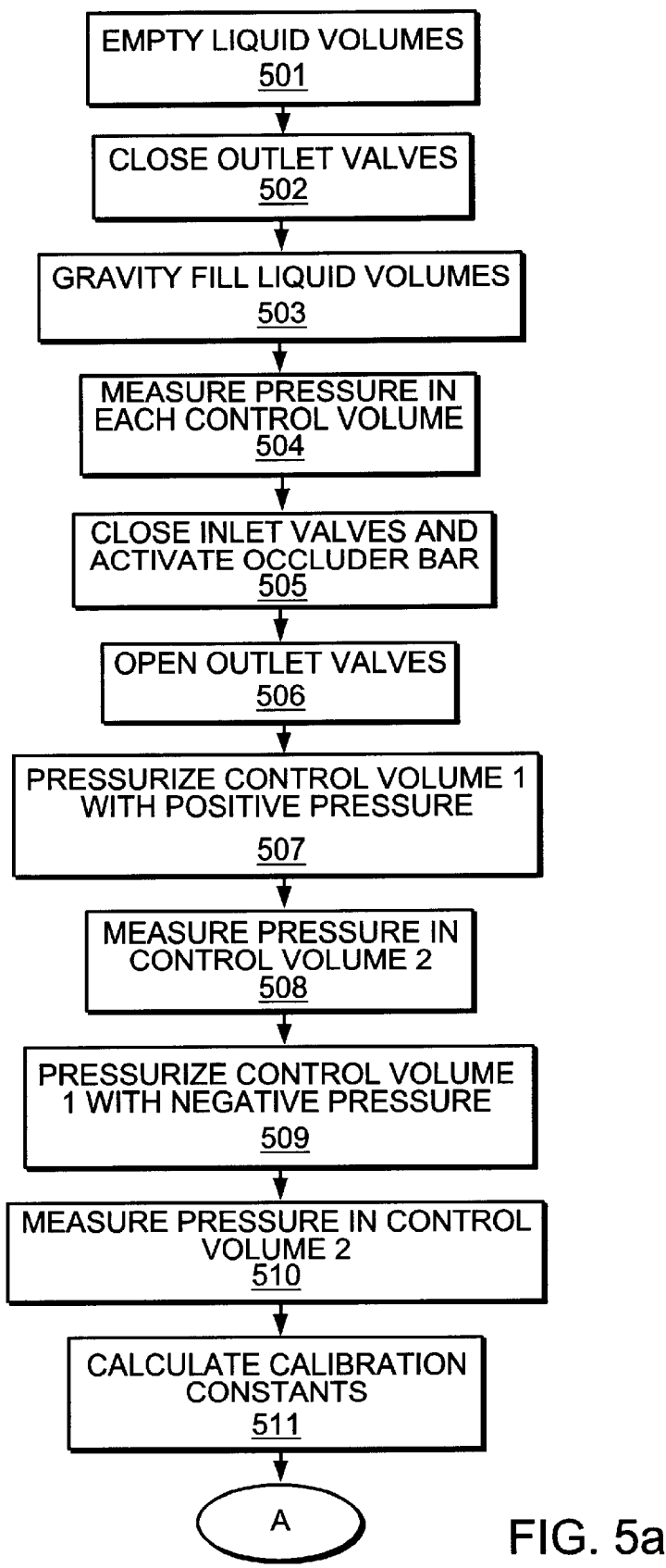
FIGS. 5(a) and 5(b) are block diagrams illustrating calibration and regulation processes according to another embodiment of the invention.

FIG. 5(a) shows a block diagram highlighting the start up and calibration procedures according to a preferred embodiment of the invention that employs the fluid flow control system of FIG. 2. The liquid volumes 302 and 312 are emptied in process 501 since either one or both volumes may be partially full from previous procedures. After both liquid volumes 302 and 312 are emptied, both outlet valves 306 and 316 are closed in process 502. Both liquid volumes 302 and 312 are gravity filled with fluid in process 503. In this embodiment, the fluid is obtained through an inlet line from heated solution bag 202 as shown in FIG. 1. Since the solution bag 202 sits on top of the fluid flow control device 200, the static head resulting from the difference in elevation between the solution bag 202 and the pumps 300 and 310 is known and small. Liquid volumes 302 and 312 are filled via gravity as solution bag 202 is located at a higher elevation than are liquid volumes 302 and 312.

The pressures in the control volumes 301 and 311 are measured in process 504 using the pressure transducers 305 and 315. A transducer may be any instrument for converting a pressure to a signal, preferably an electrical signal. The pressures measured in process 504 are to be correlated to a zero static head (or defined to be zero). Both pump inlet valves 307 and 317 are closed and the occluder bar 205 is activated in process 505. The order of closure and activation is not significant. The effect of process 505 is to isolate the fluid in the liquid volumes 302 and 312 and outlet line 204 upstream of the occluder bar 205. In process 506 both outlet valves 306 and 316 are opened. Opening both outlet valves 306 and 316 enables fluid to be pumped between the two liquid volumes 302 and 312 while keeping the total fluid volume within the liquid volumes 302 and 312 constant.

The first control volume 301 is pressurized in process 507 to a pre-selected positive pressure. The selection of. the pre-selected positive pressure is determined by factors such as the expected range of relative elevations and the dynamic range of the pressure transducers 305 and 315. The pressure in the first control volume 301 simulates a known static head. The pressure in the second control volume 311 is measured in process 508 by the pressure transducer 315.

By assuming that the two membranes are identical in their effect on pressure transmission, a relationship is derivable from the two sets of pressure measurements, and calibration constants may be calculated at this point. However, in further preferred embodiments of the invention, processes 507 and 508 are repeated. This time, the first control volume 301 is pressurized using a pre-selected negative pressure in process 509 and the pressure in the second control volume is measured in process 510. In process 511 of this embodiment, a relationship is derived from the three sets of pressure measurements, and calibration constants are calculated.

Figure 5B:
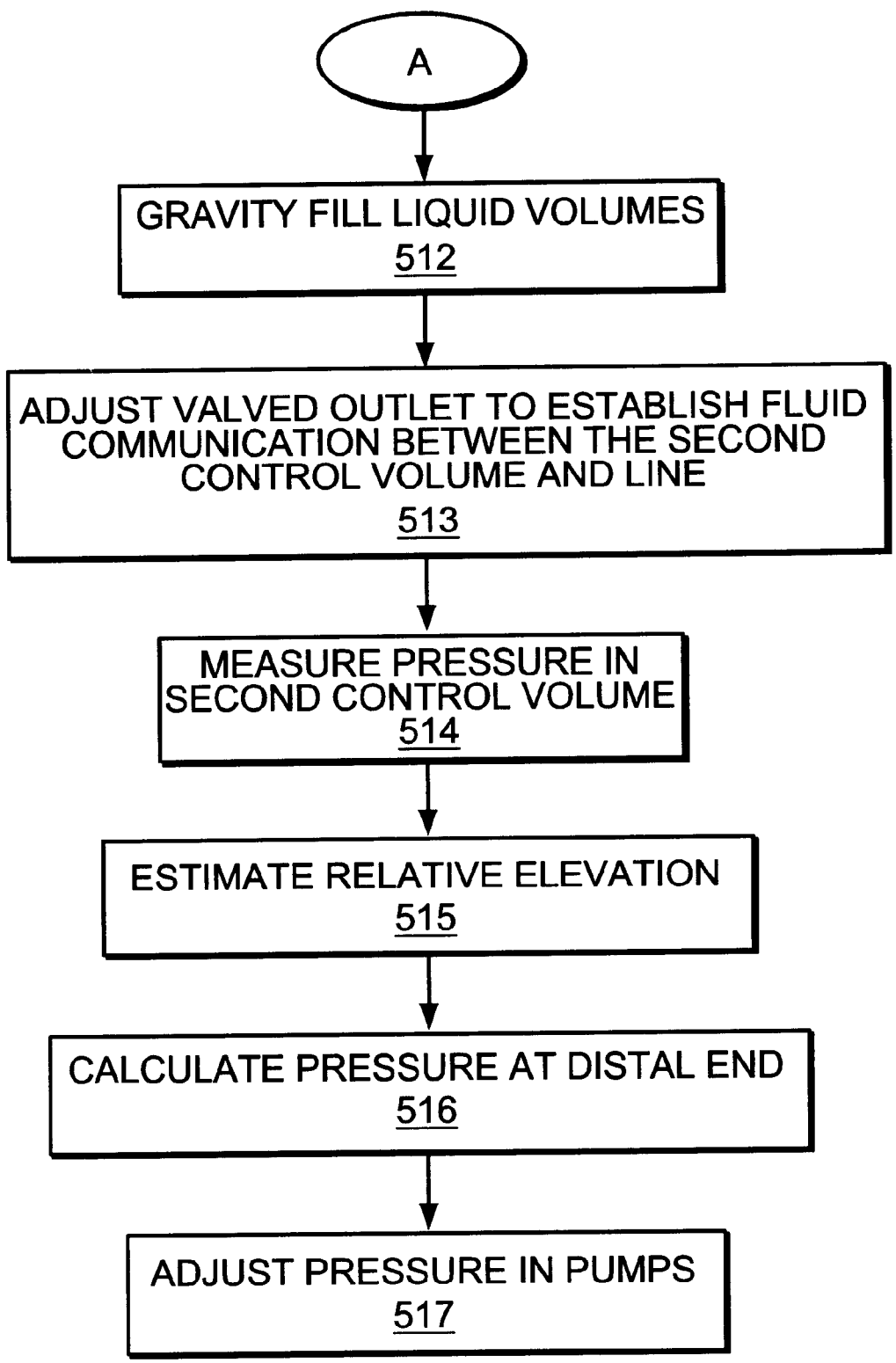

FIG. 5(b) is a block diagram illustrating the processes following the start up and calibration procedures of FIG. 5(a). In process 512 the liquid volumes 302 and 312 are again gravity filled. The valved outlet is adjusted in process 513 allowing fluid communication only between the second pump 310 and the outlet line 204. The adjustment is accomplished by emptying the first control volume 301, closing the first outlet valve 306, and deactivating the occluder bar 205. The result of these actions places the second pump 310 in fluid communication with the outlet line 204 while isolating the second pump 310 from the rest of the system. In process 514, the pressure transducer 315 measures the pressure in the second control volume 311, and the relative elevation is estimated in process 515 based on the pressure in the second control volume and the calibration constants generated during calibration.

Figure 6:
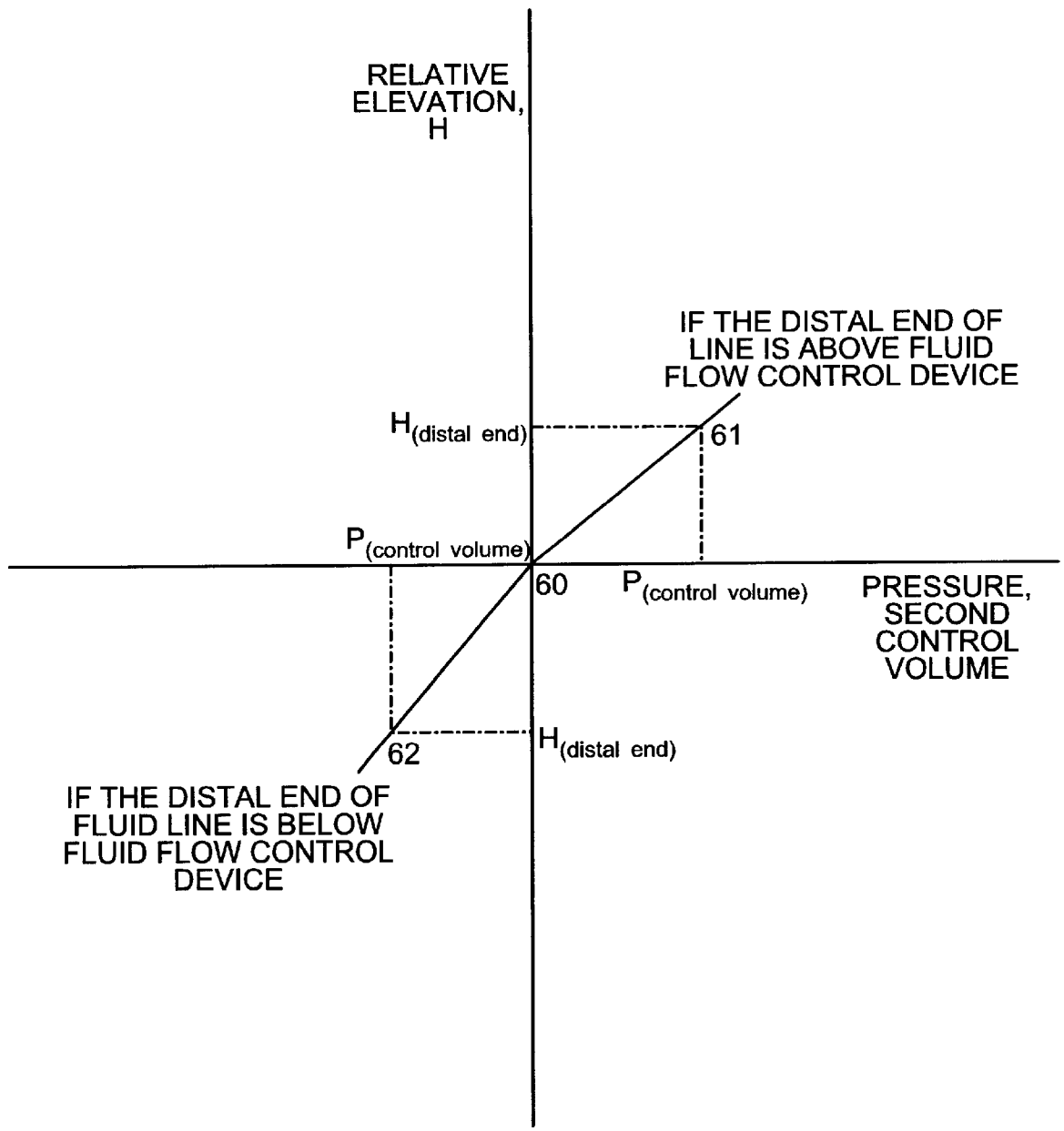
FIG. 6 is a graphical representation of the relationship derived from the process of FIG. 5.

FIG. 6 is a graphical representation of two piecewise linear fits using coordinates of relative elevation (on the ordinate) and the pressure measured in process 514, $P_{(control\ volume)}$ (on the abscissa). The head pressure may be determined from the relative elevation by the equation $p=\rho gh$, where p is the pressure, $\rho$ is the fluid density, g is the acceleration due to gravity, and h is the relative elevation. A point, H (on the ordinate), is determined by erecting a perpendicular from the $P_{(control\ volume)}$ value on the abscissa to the linear fit derived from the six calibration pressure values. Subsequently, the pressure at the distal end 208 of the fluid line 204, $P_{(distal\ end)}$ due to the elevation differential may be calculated in process 516. Finally, the pressure in the pumps 300 and 310 may be adjusted in process 517 to accommodate the height differential.

A computer program product may be employed for implementing the methods of the present invention. The computer program product comprises a computer usable medium having computer readable program code thereon. The computer readable program may include program code for reading and storing pressure values within the liquid volume 302 or 312, program code for computing and identifying correlations between stored pressure values, program code for calculating pressure values based on the identified correlations, and program code for estimating the elevation differential based upon the calculated pressures. The computer program product may also include program code for calculating a desired fluid pump pressure based upon the elevation differential and program code for adjusting the pump pressure in accordance with the desired pump pressure.

The computer program product may be run on a data processing unit, which acts as a controller. Such a unit may be capable of adjusting the flow rate of fluid being pumped to the distal end 208 by adjusting the pump pressure. For example, if the calculation determined that the distal end 208 of the fluid line 204 and the fluid control system were at the same height, the pump pressure might be safely increased above 75 mm Hg resulting in faster fluid flow rate. Further, all method processes may be performed under processor control. A memory may be provided to store upper limits on safe pressures at the distal end 208 of the line 204 based upon the elevation differential between the distal end 208 and the system. A processor capable of receiving data as to elevation differential could then calculate and control pressure levels.

Although, in the system described herein above, the liquid volumes used to determine the relative elevation are pumps containing membranes, it will appreciated that separate pumps, control volumes, and liquid volumes may be provided and that the liquid volumes and control volumes may be located at a different point from the pumps along the fluid pathway to the distal end of the fluid line. In such an embodiment, the height difference between the liquid volumes and the pumps or control volumes should be constant, so that the height difference is known. It should also be appreciated that the liquid volumes and the pressurizing means need not be at the same location, and that the first and second liquid volumes may likewise be in separate locations.

It will be further understood by one of ordinary skill in the art that other modifications can be made without departing from the spirit and the scope of the invention, as set forth in the claims below.

What is claimed is:

1. A method for regulating pressure at a distal end of a fluid line, the method comprising:

providing a fluid flow control system, the fluid flow control system having at least one liquid volume in valved communication with. the distal end, a control volume in pressure communication with the liquid volume, means for measuring pressure in the control volume, and means for adjusting the pressure in the control volume;

calibrating the means for measuring the pressure;

establishing communication between the liquid volume and the distal end;

measuring a pressure of the control volume; and adjusting the pressure in the control volume in accordance with the measured pressure.

2. A method according to claim 1, wherein the liquid volume includes a flexible membrane that separates the liquid volume from the control volume.

3. A method according to claim 1, wherein the fluid flow control system includes a pump.

4. A method for regulating pressure in a fluid line, the method comprising:

providing a fluid flow control system, the fluid flow control system having at least one liquid volume in valved communication with a distal end of a fluid line;

isolating the liquid volume from the distal end;

measuring a first calibration pressure of a control volume in pressure communication with the liquid volume;

pressurizing the liquid volume;

measuring a second calibration pressure of the control volume;

establishing communication between the liquid volume and the distal end;

measuring a pressure of the control volume; and adjusting the pressure in accordance with the measured pressure and the first and second calibration pressures.

5. A method according to claim 4, wherein the liquid volume includes a flexible membrane that separates the liquid volume from the control volume.

6. A method according to claim 4, wherein the fluid flow control system includes a pump.

7. A method for regulating pressure in a fluid line, the method comprising:

providing a fluid flow control system, the fluid flow control system having at least one liquid volume in valved communication with a distal end of a fluid line;

isolating the liquid volume from the distal end;

measuring the pressure of a control volume in pressure communication with the liquid volume;

positively pressurizing the liquid volume;

measuring the pressure of the control volume while the liquid volume is positively pressurized;

negatively pressurizing the liquid volume;

measuring a pressure of the control volume while the liquid volume is negatively pressurized;

establishing communication between the liquid volume and the distal end;

measuring the pressure of the control volume; and adjusting the pressure in accordance with the measured pressure.

8. A method according to claim 7, wherein the liquid volume includes a flexible membrane that separates the liquid volume from the control volume.

9. A method according to claim 7, wherein the fluid flow control system includes a pump.

10. A method for regulating pressure in a fluid line, the method comprising:

providing a fluid flow control system, the fluid flow control system having means for measuring pressure, a first liquid volume and a second liquid volume, the first liquid volume in valved communication with the second liquid volume;

establishing valved communication between a distal end of the fluid line and the first liquid volume and the second liquid volume;

calibrating the means for measuring pressure;

establishing communication between the first liquid volume and the distal end;

measuring a pressure of a fluid in pressure equilibrium with liquid in the first liquid volume;

adjusting the pressure in accordance with the measured pressure.

11. A method according to claim 10, wherein calibrating the means for measuring pressure comprises:

isolating the liquid volumes from the distal end;

measuring a first calibration pressure of the fluid in pressure equilibrium with liquid in the first liquid volume and a first calibration pressure of a fluid in pressure equilibrium with liquid in the second liquid volume;

pressurizing the first liquid volume;

measuring a second calibration pressure of the fluid in pressure equilibrium with liquid in the second liquid volume; and adjusting the pressure in accordance with the measured pressures.

12. A method according to claim 10, wherein calibrating the means for measuring pressure comprises:

isolating the liquid volumes from the distal end;

measuring a first calibration pressure of the fluid in pressure equilibrium with liquid in the first liquid volume and a first calibration pressure of a fluid in pressure equilibrium with liquid in the second liquid volume;

positively pressurizing the first liquid volume;

measuring a second calibration pressure of the fluid in pressure equilibrium with liquid in the second liquid volume while the first liquid volume is positively pressurized;

negatively pressurizing the first liquid volume;

measuring a third calibration pressure of the fluid in pressure equilibrium with liquid in the second liquid volume while the first liquid volume is negatively pressurized; and adjusting the pressure in accordance with the measured pressures.

13. A method according to claim 10, wherein each of the first and second liquid volumes includes a flexible membrane that separates the liquid volume from a control volume, and wherein the pressure measurements are taken from the control volume.

14. A method according to claim 10, wherein the first and second liquid volumes are disposed within a cassette.

15. A method according to claim 14, wherein the fluid flow control system includes a pump.

16. A method for regulating pressure at a distal end of a fluid line, the method comprising:

providing a fluid flow control system, the fluid flow control system having at least one liquid volume in valved communication with the distal end, a control volume in pressure communication with the liquid volume, a pressure transducer in communication with the control volume, and a pressure adjuster in communication with the control volume;

calibrating the pressure transducer;

establishing communication between the liquid volume and the distal end;

measuring a pressure of the control volume; and adjusting the pressure in the control volume in accordance with the measured pressure.

17. A method according to claim 16, wherein calibrating the pressure transducer comprises:
   isolating the liquid volume from the distal end;
   measuring a first calibration pressure of the control volume;
   pressurizing the liquid volume; and
   measuring a second calibration pressure of the control volume.

18. A method according to claim 16, wherein calibrating the pressure transducer comprises:
   isolating the liquid volume from the distal end;
   measuring the pressure of the control volume;
   positively pressurizing the liquid volume;
   measuring the pressure of the control volume while the liquid volume is positively pressurized;
   negatively pressurizing the liquid volume; and
   measuring the pressure of the control volume while the liquid volume is negatively pressurized.

19. A method according to claim 16, wherein the liquid volume includes a flexible membrane that separates the liquid volume from the control volume.

20. A method according to claim 16, wherein the fluid flow control system includes a pump.

21. A method for regulating pressure in a fluid line, the method comprising:
   providing a fluid flow control system, the fluid flow control system having a pressure transducer, a first liquid volume and a second liquid volume, the first liquid volume in valved communication with the second liquid volume;
   establishing valved communication between a distal end of the fluid line and the first liquid volume and the second liquid volume;
   calibrating the pressure transducer;
   establishing communication between the first liquid volume and the distal end;
   measuring a pressure of a fluid in pressure equilibrium with liquid in the first liquid volume;
   adjusting the pressure in accordance with the measured pressure.

22. A method according to claim 21, wherein calibrating the pressure transducer comprises:
   isolating the liquid volumes from the distal end;
   measuring a first calibration pressure of the fluid in pressure equilibrium with liquid in the first liquid volume and a first calibration pressure of a fluid in pressure equilibrium with liquid in the second liquid volume;
   pressurizing the first liquid volume;
   measuring a second calibration pressure of the fluid in pressure equilibrium with liquid in the second liquid volume; and
   adjusting the pressure in accordance with the measured pressures.

23. A method according to claim 21, wherein calibrating the pressure transducer comprises:
   isolating the liquid volumes from the distal end;
   measuring a first calibration pressure of the fluid in pressure equilibrium with liquid in the first liquid volume and a first calibration pressure of a fluid in pressure equilibrium with liquid in the second liquid volume;
   positively pressurizing the first liquid volume;
   measuring a second calibration pressure of the fluid in pressure equilibrium with liquid in the second liquid volume while the first liquid volume is positively pressurized;
   negatively pressurizing the first liquid volume;
   measuring a third calibration pressure of the fluid in pressure equilibrium with liquid in the second liquid volume while the first liquid volume is negatively pressurized; and
   adjusting the pressure in accordance with the measured pressures.

24. A method according to claim 21, wherein each of the first and second liquid volumes includes a flexible membrane that separates the liquid volume from a control volume, and wherein the pressure measurements are taken from the control volume.

25. A method according to claim 21, wherein the first and second liquid volumes are disposed within a cassette.

26. A method according to claim 25, wherein the fluid flow control system includes a pump.

* * * * *